United States Patent
Kim

(10) Patent No.: US 11,007,241 B2
(45) Date of Patent: May 18, 2021

(54) COMPOSITIONS FOR RELIEVING PAIN WITH MALKANGNI OIL AND CYPRIOL OIL AS ACTIVE INGREDIENTS AND METHOD OF TOPICAL ADMINISTRATION OF THE SAME

(71) Applicant: YSBio Co., Ltd., Seoul (KR)

(72) Inventor: You Soo Kim, Seoul (KR)

(73) Assignee: YSBio Co., Ltd., Seoul (KR)

( * ) Notice: Subject to any disclaimer, the term of this patent is extended or adjusted under 35 U.S.C. 154(b) by 0 days.

(21) Appl. No.: 16/553,919

(22) Filed: Aug. 28, 2019

(65) Prior Publication Data

US 2020/0246408 A1 Aug. 6, 2020

(30) Foreign Application Priority Data

Jan. 31, 2019 (KR) ........................ 10-2019-0013073

(51) Int. Cl.
| | |
|---|---|
| *A61K 36/00* | (2006.01) |
| *A61K 36/37* | (2006.01) |
| *A61K 8/9794* | (2017.01) |
| *A61K 8/9789* | (2017.01) |
| *A61P 29/00* | (2006.01) |
| *A61K 9/00* | (2006.01) |
| *A61K 36/8905* | (2006.01) |
| *A61K 47/44* | (2017.01) |

(52) U.S. Cl.
CPC ............ *A61K 36/37* (2013.01); *A61K 8/9789* (2017.08); *A61K 8/9794* (2017.08); *A61K 9/0014* (2013.01); *A61K 36/8905* (2013.01); *A61K 47/44* (2013.01); *A61P 29/00* (2018.01)

(58) Field of Classification Search
None
See application file for complete search history.

(56) References Cited

U.S. PATENT DOCUMENTS

2017/0056464 A1* 3/2017 Parris ..................... A61K 9/10

FOREIGN PATENT DOCUMENTS

| | | | |
|---|---|---|---|
| IN | 201303623 I1 | * | 6/2015 |
| WO | 2017072798 | | 5/2017 |

OTHER PUBLICATIONS

Extended European Search Report dated Feb. 28, 2020, issued in European Patent Application No. 19189970.7.
Alam et al, Antinociceptive and anti-hyperglycemic activity of methanol leaf extract of Cyperus scariosus, Article in Pakistan Journal of Pharmaceutical Sciences, Jan. 2011, pp. 53-56, vol. 24, Pakistan.
Kulkarni et al, Effect of Jyotishmati (Celastrus paniculatus) seeds in animal models of pain and inflammation, Article in Journal of Ayurveda & Integrative Medicine, Apr.-Jun. 2015, pp. 82-88, vol. 6, Issue 2, Mumbai, India.

* cited by examiner

*Primary Examiner* — Qiuwen Mi

(74) *Attorney, Agent, or Firm* — H.C. Park & Associates, PLC

(57) ABSTRACT

A pharmaceutical composition for treating pain including malkangni oil and cypriol oil as active ingredients, and a method of topical administration of a pharmaceutical composition on skin for relieving pain, the method including: locally applying the pharmaceutical composition on an area of skin corresponding to the pain, wherein the pharmaceutical composition including malkangni oil and cypriol oil as active ingredients.

20 Claims, 3 Drawing Sheets

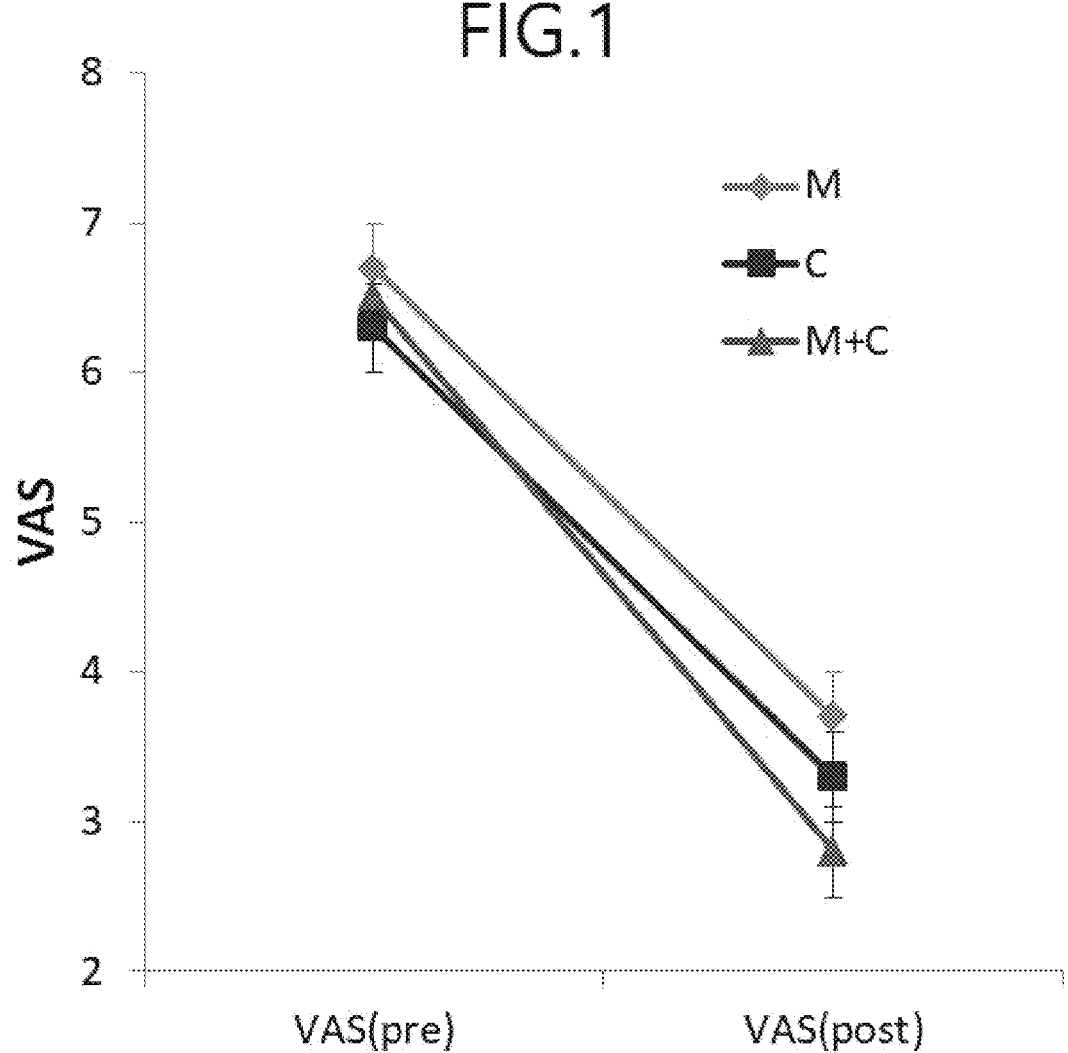

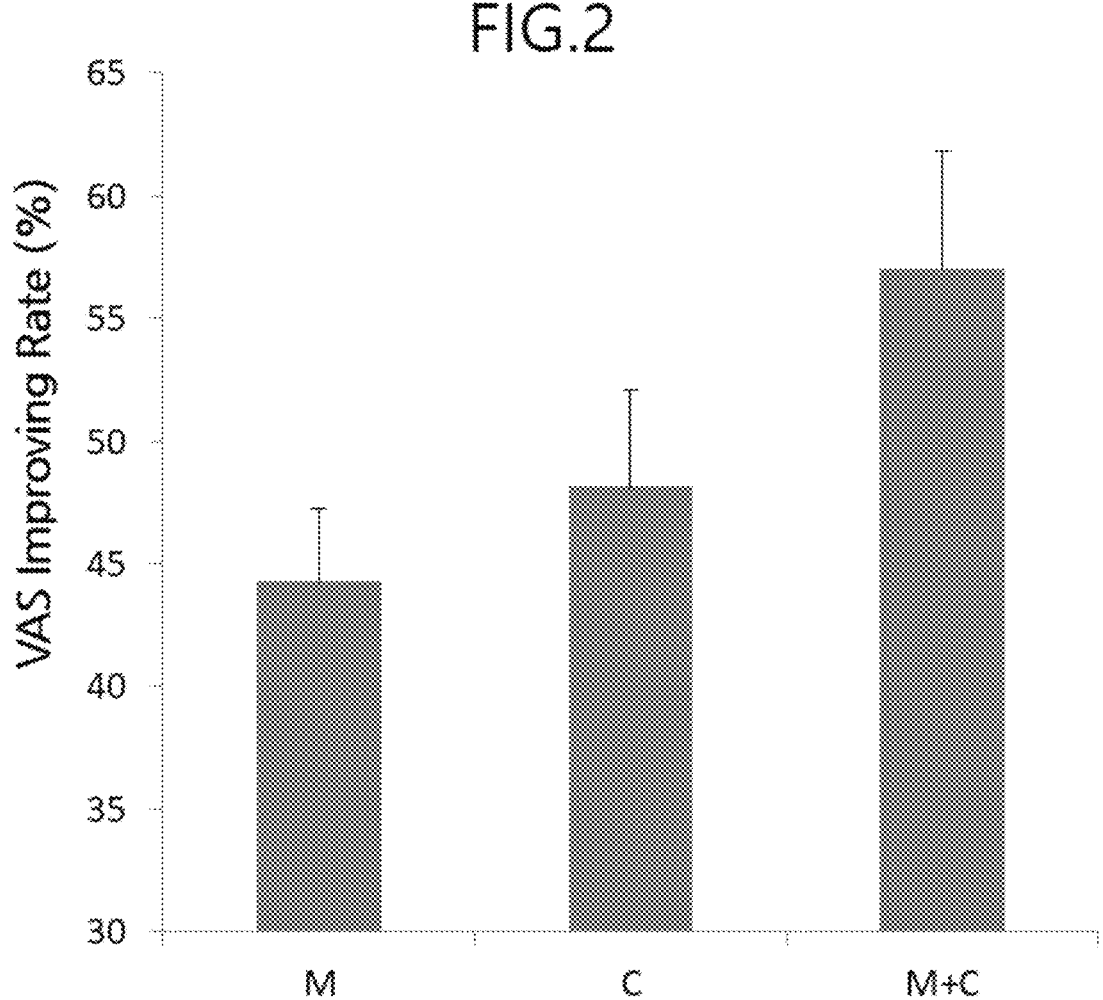

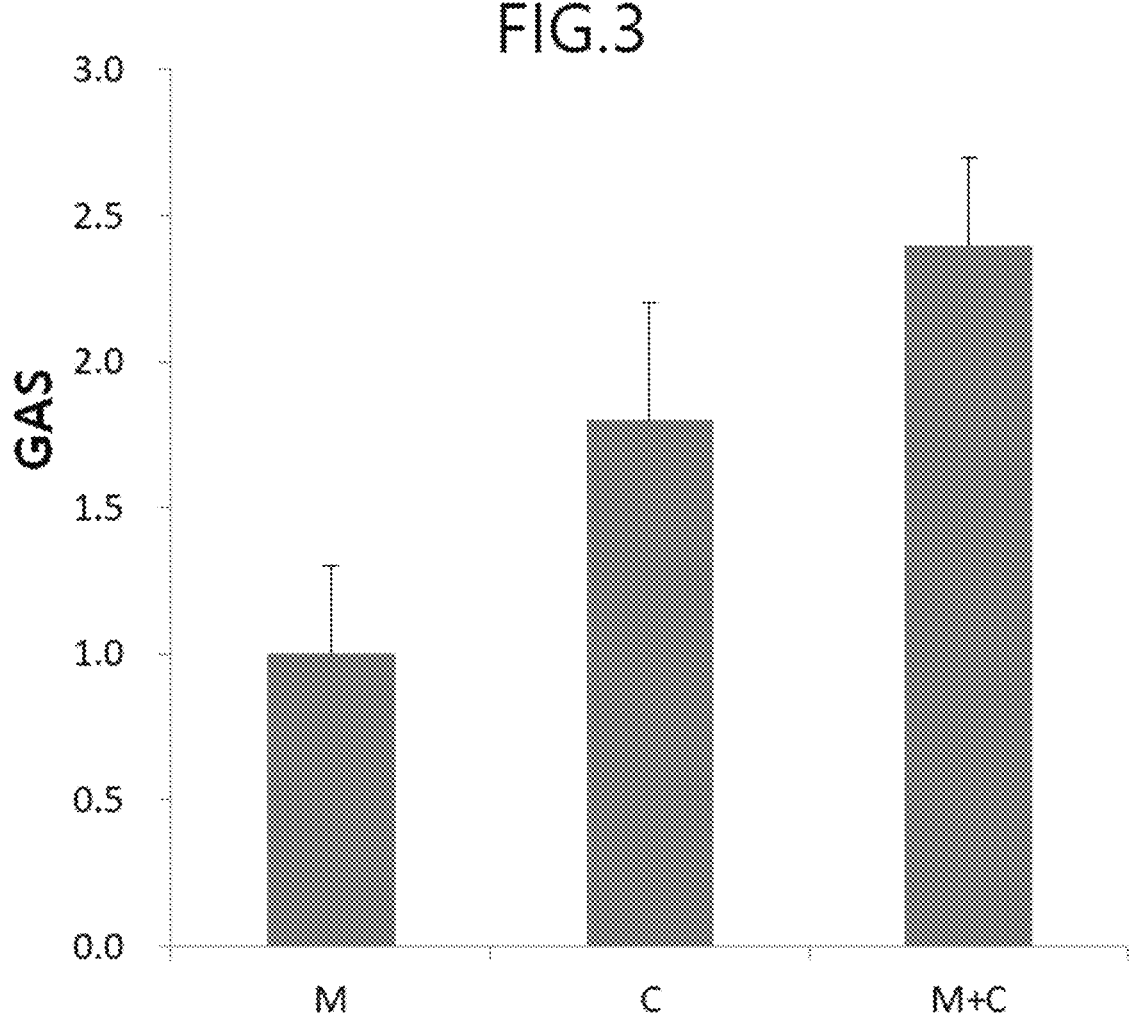

COMPOSITIONS FOR RELIEVING PAIN WITH MALKANGNI OIL AND CYPRIOL OIL AS ACTIVE INGREDIENTS AND METHOD OF TOPICAL ADMINISTRATION OF THE SAME

CROSS REFERENCE TO RELATED APPLICATION

This application claims priority from and the benefit of Korean Patent Application No. 10-2019-0013073, filed on Jan. 31, 2019, which is hereby incorporated by reference for all purposes as if fully set forth herein.

BACKGROUND

Field

Exemplary embodiments/implementations of the invention relate generally to compositions for relieving pain comprising malkangni oil and cypriol oil as active ingredients, and more specifically to a pharmaceutical composition for treating pain, a composition for skin application for relieving pain and a cosmetic composition for relieving pain, each comprising malkangni oil and cypriol oil.

Discussion of the Background

It is generally known that pain plays a vital role in protecting the body from danger and repairing damaged tissue. Pathological pain caused by viral or bacterial infections, severe inflammatory reactions around peripheral nerves, or direct damage to peripheral nerves is harmful to the human body and has a profound effect on the quality of life of the patient.

Throughout human history, analgesics for relieving pain or numbing pain have been developed and used for a long time. These analgesics act on peripheral nerves or the central nervous system to relieve pain. Analgesics can be largely divided into acetaminophen-based analgesics having only a pain-killing effect without fever relieving and anti-inflammatory effects, steroidal analgesics, non-steroidal analgesics, and narcotic analgesics such as morphine. Analgesics do not have immediate serious side-effects, but when they are administered for a long period of time, they can affect in vivo function regardless of pain, and thus they can cause damage to the body or can be addictive. For this reason, the analgesics should be carefully selected considering the degree of pain and response to other drugs.

Developments of various analgesics had been made to treat the pathologies or severities of various pains, including mild and daily pain caused by excessive use of muscles joints and severe pain caused by side effects of chemotherapy. The analgesics are generally considered safe to use for an extended period of time and not toxic.

The above information disclosed in this Background section is only for understanding of the background of the inventive concepts, and, therefore, it may contain information that does not constitute prior art.

SUMMARY

Compositions/methods according to exemplary embodiments of the invention are capable of providing a pharmaceutical composition for treating pain, and a method of topical administration of the same for treating pain.

Additional features of the inventive concepts will be set forth in the description which follows, and in part will be apparent from the description, or may be learned by practice of the inventive concepts.

According to one or more exemplary embodiments of the invention, a pharmaceutical composition for treating pain includes malkangni oil and cypriol oil as active ingredients.

A ratio of weight of the malkangni oil to weight of the cypriol oil may be 1 to 0.1 or greater and 10 or less.

The composition may further include a carrier oil.

A ratio of weight of the malkangni oil to weight of the carrier oil may be 1 to 0.1 or greater and 99 or less.

The carrier oil may include at least one selected from the group consisting of almond oil, sweet almond oil, olive oil, castor oil, jojoba oil, avocado oil, apricot kernel oil, borage oil, *Calendula* oil, carrot seed oil, cocoa butter, evening primrose oil, grape seed oil, hazelnut oil, walnut oil, pecan nut oil, macadamia nut oil, peanut oil, rosehip seed oil, sesame seed oil, flaxseed oil, sunflower seed oil, *Camellia* seed oil, manila oil, safflower oil, canola oil, soybean oil, wheat germ oil, marigold oil, lime blossom oil, coconut oil, *Arnica* oil, shea butter, and peach kernel oil.

The composition may further include a vegetable essential oil.

A ratio of weight of the malkangni oil to weight of the vegetable essential oil may be 1 to 0.1 or greater and 10 or less.

The vegetable essential oil may include at least one selected from the group consisting of *Cassia* bark oil, lemon oil, lemongrass oil, lavender oil, rosemary oil, sweet orange oil, bergamot oil, mandarin oil, star anise oil, cinnamon oil, ginger oil, *Cananga* oil, ylang ylang oil, cajeput oil, clove oil, patchouli oil, peppermint oil, spearmint oil, *Mentha arvensis* oil, frankincense oil, myrrh oil, roman chamomile oil, German chamomile oil, sweet majoram oil, geranium oil, jasmine oil, *Eucalyptus* oil, black pepper oil, and *Helichrysum* oil.

According to one or more exemplary embodiments of the invention, a cosmetic composition for relieving pain, the cosmetic composition including malkangni oil and cypriol oil as active ingredients.

According to one or more exemplary embodiments of the invention, a method of topical administration of a pharmaceutical composition on skin for relieving pain, the method including: locally applying the pharmaceutical composition on an area of skin corresponding to the pain, wherein the pharmaceutical composition including malkangni oil and cypriol oil as active ingredients.

The pain may be acute pain or chronic pain.

The pain may be associated with one or more selected from among diabetic neuropathy, diabetic peripheral neuropathy, pain caused by viral infection, nociceptive pain, facial neuralgia, postherpetic neuralgia, low back pain, disc, radiculopathy, neuropathy, hyperalgesia, central sensitization-related pain, allodynia, cancer pain, myofascial pain syndrome, Carpal tunnel syndrome, cubital tunnel syndrome (ulnar neuropathy), DeQuervain syndrome, rotator cuff syndrome, osteoarthritis, tendinitis, peritenonitis, lateral epicondylitis, medial epicondylitis, tendon injury, bursitis, syndesmitis, tennis elbow, golf elbow, knee arthralgia, tendinitis around knee, semilunar cartilage injury, finger arthralgia, wrist tendinitis, wrist sprain, ankle sprain, sprain, fibromyalgia, plantar fasciitis, inflammatory arthritis, infectious arthritis, rheumatoid arthritis, degenerative joint pain, frozen shoulder, gout, postnatal joint pain, osteomyelitis, ankylosing spondylitis, degenerative spinal lesion, lumbar spinal stenosis, cruralgia, sprain, bruise, arthralgia, and sciatica.

The pharmaceutical composition may further include a carrier oil and a vegetable essential oil.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

FIG. 1 shows visual analogue scales (VASs) before administration (VAS(pre)) and after administration (VAS(post)) of each composition.

FIG. 2 shows the improvement rates of visual analogue scales (VASs) before and after treatment with each composition.

FIG. 3 shows a global assessment scale (GAS) after administration of each composition.

DETAILED DESCRIPTION

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, etc. (hereinafter individually or collectively referred to as "elements"), of the various embodiments may be otherwise combined, separated, interchanged, and/or rearranged without departing from the inventive concepts.

For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

The exemplary embodiments provide a pharmaceutical composition for treating pain including malkangni oil and cypriol oil as active ingredients, and also a composition for skin application for relieving pain including malkangni oil and cypriol oil as active ingredients. The exemplary embodiments also provide a cosmetic composition for relieving pain including malkangni oil and cypriol oil as active ingredients.

Hereinafter, the exemplary embodiments will be described in detail.

The exemplary embodiments provides a pharmaceutical composition for treating pain including malkangni oil and cypriol oil as active ingredients. The pharmaceutical composition for treating pain according to the exemplary embodiments includes malkangni oil and cypriol oil as main active ingredients.

According to the results of a study as described in detail in an example below, a composition including malkangni oil and cypriol oil was applied locally to the painful areas of musculoskeletal pain patients, and as a result, it was confirmed that the composition including a combination of malkangni oil and cypriol oil exhibited a significantly improved pain-relieving effect compared to a composition including malkangni oil alone or a composition including cypriol oil alone. It was confirmed that the pain-relieving effect was further improved when cypriol oil and malkangni oil were co-administered compared to when cypriol oil or malkangni oil was administered alone as an active ingredient.

In another example, it was confirmed that a composition including a combination of malkangni oil and cypriol oil had improved feeling of use compared to when pure malkangni oil was used alone, and thus showed reduced skin stickiness and increased absorption rate, indicating that the composition has further improved use feeling and sensory properties. It can be seen that when malkangni oil in the composition according to the exemplary embodiments is suitably blended with a carrier oil, the composition can more effectively exhibit a pain-relieving effect by increasing the skin penetration of the active ingredients compared to when pure malkangni oil is used alone, even though the content of the malkangni oil decreases.

Therefore, it can be seen that the composition including a combination of malkangni oil and cypriol oil can be used to develop a composition for treating or relieving pain, which is safe, has little or no side effects, and has a pain relieving effect which is much higher than that of malkangni oil or cypriol oil.

As used herein, the term "malkangni oil" refers to an oil extracted from the seed of *Celastrus paniculatus*, a plant belonging to the genus *Celastrus*. *Celastrus paniculatus* is known to have sharp and bitter taste and have the property of generating fever. As used herein, the term "malkangni oil" is meant to include an oil obtained by directly pressing the seed of *Celastrus paniculatus*, or an oil obtained by preparing a seed extract using a solvent such as an organic solvent and diluting the extract in a suitable oil. Malkangni oil which is used in the practice of the exemplary embodiments is an oil extracted by a cold-pressing technique so as to the loss or alteration of specific components contained in malkangni oil.

As used herein, the term "cypriol oil" refers to an essential oil extracted from the tuber of *Cyperus scariosus*, a perennial plant of the *Cyperus*, which is distributed in temperate and tropical areas. It is a brown viscous liquid with a wood or soil-like flavor.

The composition according to the exemplary embodiments may include malkangni oil and cypriol oil at a weight ratio of 1:0.1 to 10, more particularly 1:2, but is not limited thereto.

The composition according to the exemplary embodiments may further include a 'carrier oil'. The composition according to the exemplary embodiments may include the carrier oil in order to develop a topical formulation or a formulation for skin external application for administering the composition via the rough through which the composition is absorbed into the skin.

The carrier oil in the specification is also referred to as a base oil or a fixed oil, and is used to apply a volatile essential oil or a 100% pure substance to the skin or the like or to prepare a fragrance composition by diluting this oil or substance. The carrier oil is mainly vegetable oil, and is most preferably is in its natural pure state, which contains no other components or is non-deteriorated state. Particular types of carrier oils have a unique flavor, but most of them have no flavor, no volatility, and are somewhat viscous. The viscosity of carrier oil, the extent to which it is easily applied to the skin, and the extent to which it is absorbed into the skin vary depending on the type of carrier oil. The carrier oil should be chosen considering whether it can stably maintain the component to be diluted (e.g., essential oil), or whether it enables the component to penetrate the skin well, or whether the carrier oil has an effect or activity.

When the composition according to the exemplary embodiments includes the carrier oil, the composition may include malkangni oil, cypriol oil and the carrier oil at a weight ratio of 1:0.1 to 10:0.1 to 99.

The composition according to the exemplary embodiments may include one type of carrier oil, or may include a mixture of two or more types of selected carrier oils. Specifically, an example of carrier oils which may be selected for addition to the composition of the exemplary embodiments may be one or more selected from the group consisting of almond oil, sweet almond oil, olive oil, castor oil, jojoba oil, avocado oil, apricot kernel oil, borage oil, *Calendula* oil, carrot seed oil, cocoa butter, evening primrose oil, grape seed oil, hazelnut oil, walnut oil, pecan nut oil, macadamia nut oil, peanut oil, rosehip seed oil, sesame seed oil, flaxseed oil, sunflower seed oil, *Camellia* seed oil, marula oil, safflower oil, canola oil, soybean oil, wheat germ oil, marigold oil, lime blossom oil, coconut oil, *Arnica* oil, shea butter, and peach kernel oil.

Among the above-described types of carrier oils, almond oil, sweet almond oil or jojoba oil is preferably used at the weight ratio proposed in the exemplary embodiments so that the composition including malkangni oil and cypriol oil according to the exemplary embodiments will be easily applied to the skin without stickiness and quickly absorbed into the skin and a subcutaneous painful area, thus increasing the pain killing effect. Jojoba oil has advantages in that it is similar to human skin ingredients, and has excellent skin penetration ability, is less sticky, and is less prone to rancidity than other carrier oils. In addition, sweet almond oil is rich in nutrients such as vitamin E and D, minerals, and has excellent skin absorption properties. In contrast, when other carrier oil is used, like when only a pure olive oil is used at a high concentration, the proportion of the oil that remains on the surface of the skin is higher than that of the oil that penetrates into the skin, making the skin greasy, and the oil merely acts as a sealant to inhibit moisture evaporation from the skin. In this case, the feeling of use is relatively low, making it difficult to commercialize the composition as a product.

Furthermore, a mixture of sweet almond oil and jojoba oil may most preferably be used. In this case, the weight ratio between sweet almond oil and jojoba oil is preferably selected in the range of 1:0.1 to 10 to improve the skin absorption and application properties of the composition.

In addition, the composition according to the exemplary embodiments may further include, in addition to cypriol oil, one or more vegetable essential oils.

As used herein, the term "essential oil" refers to a concentrated hydrophobic liquid including a volatile substance, such as an aromatic substance, extracted from a plant. Although essential oil is called oil, it evaporates completely at room temperature, leaving no trace, unlike fatty oils. Essential oils can be generally obtained by steam distillation, solvent extraction, cold pressing, or the like. Essential oil is known to exhibit holistic healing effects by increasing the body's resilience through mental and physical stabilization based on its anti-inflammatory, antimicrobial, antifungal, antiviral, relaxing, antidepressant, anti-anxiety and neuroprotective actions, and also functions to improve the feeling of use due to its unique fragrance.

When the composition according to the exemplary embodiments further includes a vegetable essential oil, this composition may include malkangni oil, cypriol oil and the vegetable essential oil at a weight ratio of 1:0.1 to 10:0.1 to 10.

A vegetable essential oil which may be selected for addition to the composition of the exemplary embodiments may be one or more selected from the group consisting of *Cassia* bark oil, lemon oil, lemongrass oil, lavender oil, rosemary oil, sweet orange oil, bergamot oil, mandarin oil, star anise oil, cinnamon oil, ginger oil, *Cananga* oil, ylang ylang oil, cajeput oil, clove oil, patchouli oil, peppermint oil, spearmint oil, *Mentha arvensis* oil, frankincense oil, myrrh oil, roman chamomile oil, German chamomile oil, sweet majoram oil, geranium oil, jasmine oil, *Eucalyptus* oil, black pepper oil, and *Helichrysum* oil.

In addition, the composition according to the exemplary embodiments may be a composition including malkangni oil, cypriol oil, a carrier oil and other vegetable essential oil, and in this case, the composition may include malkangni oil, cypriol oil, a carrier oil and other vegetable essential oil at a weight ratio of 1:0.1 to 10:0.1 to 99:0.1 to 10.

As used herein, the term "treatment" or "treating" refers to inhibiting occurrence or recurrence of disease, alleviating symptoms, reducing direct or indirect pathological consequences of disease, reducing the rate of disease progression, improving, bettering, or relieving disease conditions, or improving prognosis.

In addition, as used herein, the term "pain" refers to an unpleasant sensory and emotional experience caused by actual or potential tissue damage or intense external stimulation. The pain according to the exemplary embodiments may be acute or chronic pain.

The composition according to the exemplary embodiments is applicable to pain originating from the skin or musculoskeletal system. Specifically, the pain refers to pain associated with one or more selected from among diabetic neuropathy, diabetic peripheral neuropathy, pain caused by viral infection, nociceptive pain, facial neuralgia, postherpetic neuralgia, low back pain, disc, radiculopathy, neuropathy, hyperalgesia, central sensitization-related pain, allodynia, cancer pain, myofascial pain syndrome, Carpal tunnel syndrome, cubital tunnel syndrome (ulnar neuropathy), DeQuervain syndrome, rotator cuff syndrome, osteoarthritis, tendinitis, peritenonitis, lateral epicondylitis, medial epicondylitis, tendon injury, bursitis, syndesmitis, tennis elbow, golf elbow, knee arthralgia, tendinitis around knee, semilunar cartilage injury, finger arthralgia, wrist tendinitis, wrist sprain, ankle sprain, sprain, fibromyalgia, plantar fasciitis, inflammatory arthritis, infectious arthritis, rheumatoid arthritis, degenerative joint pain, frozen shoulder, gout, postnatal joint pain, osteomyelitis, ankylosing spondylitis, degenerative spinal lesion, lumbar spinal stenosis, cruralgia, sprain, bruise, arthralgia, and sciatica.

Meanwhile, since the most suitable administration route for exhibiting the pain killing effect of the composition according to the exemplary embodiments is absorption through the skin, the composition can most effectively relieve the pain of the skin tissue located close to the skin, particularly the pain of tissue with thin subcutaneous fat. That is, a preferred example of the pain is a pain associated with a sprain of an area, knee, elbow, finger, shoulder, ankle or feet, bruise, arthralgia, tendinitis, syndesmitis, frozen shoulder, rotator cuff disease, tennis elbow, golf elbow, or DeQuervain syndrome.

The pharmaceutical composition according to the exemplary embodiments may include only malkangni oil and cypriol oil, or may further include one or more pharmaceutically acceptable carriers, excipients or diluents. The term "pharmaceutically acceptable" means a non-toxic composition that is physiologically acceptable and, when administered to a human, does not inhibit the action of the active ingredient and does not commonly cause an allergic reaction such as gastrointestinal disorder, dizziness, or a similar reaction.

The pharmaceutically acceptable carriers include all kinds of solvents, dispersion media, oil-in-water or water-in-oil emulsions, aqueous compositions, liposomes, microbeads and microsomes. Depending on the route of administration, the composition may further include a carrier for oral administration or a carrier for parenteral administration. Examples of the carrier for oral administration include lactose, starch, cellulose derivatives, magnesium stearate, stearic acid, and the like. Additionally, it may include various drug delivery materials used for oral administration for peptide formulations. In addition, the carrier for parenteral administration may contain water, suitable oil, saline, aqueous glucose and glycol, and the composition may further include a stabilizer and a preservative. Suitable stabilizers include antioxidants, such as sodium hydrogen sulfite, sodium sulfite or ascorbic acid. Suitable preservatives include benzalkonium chloride, methyl- or propyl-paraben and chlorobutanol.

The pharmaceutical composition of the exemplary embodiments may further include, in addition to the above-described components, a lubricant, a wetting agent, a sweetener, a flavoring agent, an emulsifying agent, a suspending agent and the like. Other pharmaceutically acceptable carriers and their formulations are described in Remington's Pharmaceutical Sciences, $19^{th}$ ed., Mack Publishing Company, Easton, Pa., 1995.

The composition of the exemplary embodiments may be administered to mammals, including humans, by any method. For example, it may be administered orally or parenterally. Parenteral administration methods include, but are not limited to, intravenous, intramuscular, intraarterial, intramedullary, intrathecal, intracardiac, transdermal, subcutaneous, intraperitoneal, intranasal, enteral, topical, sublingual or rectal administration. For the pain relieving effect of the composition according to the present invention, the composition is preferably administered via a route, such as a transdermal or topical route, by which it is absorbed into the body through the skin.

The pharmaceutical composition of the exemplary embodiments may be formulated into formulations for oral administration or parenteral administration depending on its administration route.

Formulations for parenteral administration may be prepared in the form of injectable solution, cream, lotion, ointment for external use, oil, roll-on, moisturizer, gel, aerogel and nasal inhaler by any method known in the art. These formulations are described in Remington's Pharmaceutical Science, $19^{th}$ ed., Mack Publishing Company, Easton, Pa., 1995, which is a formulary commonly known in all pharmaceutical chemistries.

In addition, for parenteral administration, the pharmaceutical composition of the exemplary embodiments may be formulated with suitable parenteral carriers according to methods known in the art to provide injectable solutions, transdermal formulations or nasal inhalers. In particular, transdermal formulations include roll-on formulations, ointments, creams, lotions, gels, formulations for external use, pastes, liniments, aerosols, and the like. As used herein, the term "transdermal administration" means administering the pharmaceutical composition topically to the skin so that the effective amounts of the active ingredients contained in the pharmaceutical composition are delivered into the skin. For example, the pharmaceutical composition of the exemplary embodiments may be formulated into an injectable formulation, and may be administered by lightly pricking the skin with a 30 gauge syringe needle or directly applying it to the skin. These formulations are described in Remington's Pharmaceutical Science, 15th Edition, Mack Publishing Company, Easton, Pa., 1975, which is a formulary commonly known in the pharmaceutical chemistry.

For an inhalation formulation, the compounds for use according to the exemplary embodiments can be conveniently delivered in the form of an aerosol spray from a pressurized pack or nebulizer with a suitable propellant, for example, dichlorodifluoromethane, trichlorofluoromethane, dichlorotetrafluoromethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated to contain a powder mix of the compound and a suitable powder base such as lactose or starch.

In addition, the pharmaceutical composition according to the exemplary embodiments may further include one or more buffers (e.g., saline or PBS), a carbohydrate (e.g., glucose, mannose, sucrose or dextran), an antioxidant, a bacteriostatic, a chelating agent (e.g., EDTA or glutathione), an adjuvant (e.g., aluminum hydroxide), a suspending agent, a thickening agent, and/or a preservative.

The total effective amount of the composition of the exemplary embodiments may be administered to a patient in a single dose, or administered by a fractionated treatment protocol, in which multiple doses are administered over a prolonged period of time. The contents of the active ingredients in the pharmaceutical composition of the exemplary embodiments may vary depending on the severity of disease. Preferably, the preferred total dose of the pharmaceutical composition of the exemplary embodiments may be about 0.01 µg to 10,000 mg/day/kg of patient body weight, most more particularly 0.1 µg to 500 mg/day/kg of patient body weight. A roll-on formulation for transdermal administration may be prepared such that it may be applied 2 to 3 times (about 0.2 to 1.0 ml) a day. However, the dose of the pharmaceutical composition may be determined depending on various factors, including the formulation method, the route of administration, and the number of treatments, as well as the patient's age, weight, health condition, sex, the severity of the disease, the diet and the rate of excretion. In view of these factors, those skilled in the art can determine the appropriate effective dose of the composition of the present invention. The pharmaceutical composition according to the exemplary embodiments is not particularly limited in terms of its formulation, administration route, and administration method, as long as it exhibits the effect of the present invention.

In addition, the pharmaceutical composition of the exemplary embodiments may be formulated using a method known in the art so as to provide the quick, sustained or delayed release of the active ingredients after administration to humans or mammals.

Furthermore, the pharmaceutical composition of the exemplary embodiments may be administered alone or co-administered with a known compound having a pain relieving effect.

The exemplary embodiments also provides a composition for skin application (for example. external skin application) for relieving pain including malkangni oil and cypriol oil as active ingredients.

The composition for skin application according to the exemplary embodiments includes malkangni oil and cypriol oil as active ingredients and may include a pharmaceutically acceptable carrier. In addition, it may further include additives that are generally used in the skin science field, such as lipids, organic solvents, solubilizers, thickening agents, concentrating agents, gelling agents, softeners, antioxidants, suspending agents, stabilizers, foaming agents, aromatics, surfactants, water, ionic or non-ionic emulsifiers, fillers, sequestering agents, chelating agents, preservatives, vitamins, UV blocking agents, wetting agents, essential oils, dyes, pigments, hydrophilic or lipophilic activators, liposomes, or any other components. In addition, these components may be introduced in amounts that are generally accepted in the skin science field.

The dose of malkangni oil and cypriol oil in the composition for skin application may be administered at a dose of 0.0001 to 1000 mg/kg, more particularly 0.001 to 100 mg/kg, but is not limited thereto. The dose may vary depending on various factors, including the patient's weight, age, sex, health condition, the period of administration, the rate of excretion, the severity of disease, etc.

Formulation forms of the composition for skin application include, for example, but are not limited to, liquids, sprays, lotions, gels, pastes, ointments, aerosols, powders, patches, creams, roll-on, transdermal delivery systems, and so on.

A pharmaceutically acceptable carrier in the composition for skin application according to the exemplary embodiments varies depending on the formulation of the composition, and examples thereof include hydrocarbons, such as Vaseline, liquid paraffin, and plasticized hydrocarbon gel (plastibase); animal and vegetable oils, such as heavy-chain fatty acid triglyceride, lard, hard fat, and cacao butter; higher fatty acid alcohols, fatty acids and esters thereof, such as cetanol, stearyl alcohol, stearic acid and isopropyl palmitate; water-soluble bases, such as polyethylene glycol, 1,3-butylene glycol, glycerol, gelatin, white sugar, and sugar alcohol; emulsifiers, such as glycerine fatty acid ester, polyoxyl stearate, and polyoxyethylene hydrogenated castor oil; thickeners, such as acrylic acid ester and sodium alginate; propellants such as liquefied petroleum gas and carbon dioxide; and preservatives, such as paraoxybenzoic acid esters. In addition to these carriers, additives such as stabilizers, pigments, coloring agents, pH adjusting agents, diluents, surfactants, preservatives and antioxidants may, if necessary, be added to the composition for skin application. The composition for skin application according to the exemplary embodiments is applied to an affected part or a painful skin area.

In addition, the composition for skin application according to the exemplary embodiments may be used for adhesion to a solid support such as the wound release cover of a sticking plaster. The adhesion can be achieved by saturating the solid support with the composition of the exemplary embodiments and then dehydrating the composition. Preferably, the solid support may be coated with an adhesive agent to improve the adhesion of the composition of the exemplary embodiments to the solid support. Examples of the adhesive agent include polyacrylate and cyanoacrylate. Examples of this type of formulation include sticking plasters having a non-adhesive wound release cover in the form of perforated plastic film (Smith & Nephew Ltd.); thin strips, patches, spots, or plastic strip shaped BAND-AID® commercially available from Johnson & Johnson; CURITY CURAD® Ouchless adhesive plaster commercially available from Colgate-Palmolive Co. (Kendall); and STIK-TITE® (elastic strip) commercially available from American White Cross Laboratories, Inc. The composition of the exemplary embodiments may be applied as an active ingredient in this type of formulation.

The exemplary embodiments also provides a cosmetic composition for relieving pain including malkangni oil and cypriol oil as active ingredients.

The cosmetic composition according to the exemplary embodiments may be prepared into any conventional formulation known in the art. The composition according to the exemplary embodiments may be formulated with a dermatologically acceptable medium, base, adjuvant and/or excipient to provide formulations for topical application or systemic application which are generally known in the skin science field. For example, the composition of the exemplary embodiments may be prepared into basic cosmetic formulations (facial cleansers such as face lotion, cream, essence, cleansing foam and cleansing water; pack, and body oil), color cosmetic formulations (foundation, lipstick, mascara, and makeup base), hair product products (shampoo, rinse, hair conditioner, and hair gel), and soap.

In addition, the cosmetic composition of the exemplary embodiments may further include, in addition to malkangni oil and cypriol oil, additives that are generally used in the cosmetic science or skin science field, such as lipids, organic solvents, solubilizers, thickening agents, concentrating agents, gelling agents, softeners, antioxidants, suspending agents, stabilizers, foaming agents, aromatics, surfactants, water, ionic or non-ionic emulsifiers, fillers, sequestering agents, chelating agents, preservatives, vitamins, UV blocking agents, wetting agents, essential oils, dyes, pigments, hydrophilic or lipophilic activators, liposomes, or any other components. In addition, these components may be introduced in amounts that are generally accepted in the skin science field.

Examples of the excipients include, but are not limited to, skin softeners, skin penetration enhancers, coloring agents, aromatics, emulsifiers, softening agents, concentrating agents, gelling agents, suspending agents, stabilizing agents, foaming agents, surfactants, fillers or solvents. In addition, the cosmetic composition of the exemplary embodiments may further include a fragrance, a pigment, a sterilizing agent, an antioxidant, a preservative, an additive and a moisturizer, and include a thickener, an inorganic salt, a synthetic polymer and the like for the purpose of improving physical properties. For example, when the cosmetic composition of the exemplary embodiments is formulated into a facial cleanser or soap, the facial cleanser or soap may be prepared by adding the active ingredients of the exemplary embodiments to a conventional facial cleanser or soap base. When cream is prepared, it may be prepared by adding the active ingredients of the exemplary embodiments to a conventional oil-in-water cream base. In addition, the cosmetic composition of the exemplary embodiments may further include a fragrance, a chelating agent, a pigment, an antioxidant, a preservative and the like, and include synthetic or natural materials, such as proteins, minerals, and vitamins, in order to improve physical properties.

Preferably, the cosmetic composition of the exemplary embodiments may be provided in the form of, for example, a solution, a gel, a solid or pasty anhydrous product, an emulsion obtained by dispersing an oil phase in a water phase, a suspension, a microemulsion, a microcapsule, a microgranulocyte, or an ionic (liposomal) or non-ionic vesicle dispersing agent, or may also be provided in the form of cream, toner, lotion, powder, ointment, spray, or conceal stick. In addition, the cosmetic composition of the exemplary embodiments may also be prepared as a foam composition or an aerosol composition further including a compressed propellant.

Products to which the cosmetic composition of the exemplary embodiments include, but are not limited to, formulations, such as skin lotion, skin softener, skin toner, astringent lotion, skin lotion, milk lotion, astringent, lotion, moisturizer lotion, nourishing lotion, body cream, massage cream, nourishing cream, moisturizer cream, hand cream, essence, nourishing essence, pack, soap, shampoo, cleansing foam, cleansing lotion, cleansing cream, body lotion, body cleanser, treatment, cosmetic solution, emulsion, pressed powder, loose powder, and eye shadow.

The content of the active ingredients in the cosmetic composition of the exemplary embodiments may be 0.0001 to 50 wt %, more particularly 0.01 to 10 wt %, based on the total weight of the cosmetic composition.

The exemplary embodiments also provide a composition for skin application for relieving pain including malkangni oil and cypriol oil as active ingredients, and a cosmetic composition for relieving pain including malkangni oil and cypriol oil as active ingredients.

The detailed result of the experimental example of comparing of Pain-Relieving Effects between Compositions Including Malkangni Oil and/or Cypriol Oil will be provided below with reference to FIGS. 1, 2, and 3.

FIG. 1 shows visual analogue scales (VASs) before administration (VAS(pre)) and after administration (VAS (post)) of each composition. In FIG. 1, M indicates a patient group administered with a composition including malkangni oil alone; C indicates a patient group administered with a composition including cypriol oil; and M+C indicates a patient group administered with a composition including a combination of malkangni oil and cypriol oil. Error bar represents a standard error.

FIG. 2 shows the improvement rates of visual analogue scales (VASs) before and after treatment with each composition. In FIG. 2, M indicates a patient group administered with a composition including malkangni oil alone; C indicates a patient group administered with a composition including cypriol oil; and M+C indicates a patient group administered with a composition including a combination of malkangni oil and cypriol oil. Error bar represents a standard error.

FIG. 3 shows a global assessment scale (GAS) after administration of each composition. In FIG. 3, M indicates a patient group administered with a composition including malkangni oil alone; C indicates a patient group administered with a composition including cypriol oil; and M+C indicates a patient group administered with a composition including a combination of malkangni oil and cypriol oil. Error bar represents a standard error.

1. Experimental Method (1) Preparation of Experimental Compositions

In an experiment on comparison of the pain-relieving effect, the following compositions were used: a composition including malkangni oil (100%) alone (referred to as M); a composition including a combination of malkangni oil and cypriol oil (referred to as M+C); and a composition including cypriol oil alone (referred to as C). As the composition (M) including malkangni oil alone, 100% malkangni oil 100% was used without dilution. The composition (M+C) including a combination of malkangni oil and cypriol oil was prepared by stirring malkangni oil, cypriol oil and a carrier oil (an oil mixture of sweet almond oil and jojoba oil) in an agitator at 60 rpm for 30 minutes such that the contents of these oils were 5 wt %, 10 wt % and 85 wt %, respectively, based on the total weight of the composition. The cypriol oil composition (C) was prepared by stirring cypriol oil and a carrier oil in an agitator at 60 rpm for 30 minutes such that the contents of these oils were 15 wt % and 85 wt %, respectively, based on the total weight of the composition. When the cypriol oil composition (C), a vegetable essential oil, is used alone, it strongly irritates the skin, indicating that it cannot be used as a 100% pure essential oil. For this reason, for comparison of the effect of the cypriol oil composition (C) with the effect of the composition (M+C), the composition (C) was prepared such that the content of cypriol oil therein was the same as the content of malkangni oil and cypriol oil (15 wt %) in the M+C composition.

(2) Comparison of Pain-Relieving Effect between Compositions

On male and female patients who visited a Seoul Rehabilitation Clinic (Seoul, Korea) due to a musculoskeletal pain associated with tennis elbow, knee arthralgia, wrist tendinitis, DeQuervain syndrome, finger arthralgia, rotator cuff damage, and the like, the pain-relieving effects of the compositions prepared as described above were compared. For each patient, 0.3 ml of each of the three prepared compositions was randomly applied to a painful area 2 to 3 times a day, 2 to 3 days in a week, and then absorbed into the skin by scrubbing. Pains before and after application of each composition were examined by visual analogue scale (VAS), and after treatment, global assessment scale (GAS), side effects and the feeling of use were examined.

The VAS is a method that records the left end of a 10 cm ruler as 0 (no pain) and the right end as 10 (the greatest pain). In GAS, changes in the pain felt by the patients were rated on the following 9-point scales: '−4 (100% worsened)', '−3 (75% worsened)' '−2 (50% worsened)', '−1 (25% worsened)', '0 (no change)', '1 (25% improved)', '2 (50% improved)', '3 (75% improved)', '4 (100% improved)'. The index of use feeling was selected from point 0 and point 5, but was measured on a 3-point scale. Stickiness was rated on a 6-point scale: point 0='no stickiness', and 5='very sticky'. Skin absorption was rated between 0 and 5: 0='not absorbed'; and 5: 'very well absorbed'. The index of overall use feeling was rated between 0 and 5: 0='very discomfortable'; and 5='very good'. The VAS was measured once before start and after completion of the test, and the GAS and the index of use feeling were measured once after completion of the test.

2. Experimental Results (1) Comparison of Visual Analogue Scale (VAS) of Pain between Before and After Administration of Compositions and Comparison of Global Assessment Scale (GAS)

In order to discover new natural oils and a combination thereof, which can easily and quickly act on a painful area after application to the skin and exhibit a pain-relieving effect, malkangni oil and cypriol oil were selected and the pain-relieving effects thereof were examined. The pain-relieving effects of the composition (M) including malkangni oil, the cypriol oil composition (C), and the composition (M+C) including a combination of malkangni oil and cypriol oil, which were prepared as described in the Experimental Method above, were comparatively compared in musculoskeletal pain patients. The musculoskeletal pain patients were patients who visited the hospital due to wrist, ankle and elbow pains, including pains associated with ankle sprain, DeQuervain syndrome, tennis elbow, and the like. Table 1 below shows the number of patients administered with each composition, the period of administration, visual analogue scales before and after the test (VAS(pre) and VAS(post), respectively), global assessment scale (GAS) measured after completion of the test.

The period of administration and the visual analogue scale before administration (before the start of the test) were all similar between the patient groups administered with each composition. The composition (M) including malkangni oil and the cypriol oil composition (C) all showed reduced VAS values, indicating that these compositions have a pain-relieving effect. Meanwhile, the composition (M+C) including a combination of malkangni oil and cypriol oil showed the greatest decrease in the VAS value (an about 60% decrease after the test compared to before the test) among the three compositions, indicating that it has the highest pain-relieving level (see Table 1 and FIGS. 1 and 2).

In particular, the composition (M+C) showed a better effect than the composition (M) including malkangni oil alone, even though it contained a significantly smaller amount of malkangni oil and the total content of malkangni oil and cypriol oil therein was only 15 wt %. When each of the two compositions was applied to affected parts, the composition (M+C) was mostly absorbed into the skin immediately after application and did not substantially remain on the skin, and the patients administered with the composition (M+C) showed a tendency to report the pain-relieving effect within a short time. On the other hand, the composition including malkangni oil alone was very sticky due to its high viscosity (see Table 2), and the amount thereof remaining on the skin was large even after it was applied to the affected part and rubbed. Therefore, it is concluded that the composition (M+C) according to the exemplary embodiments greatly improves the skin absorption ability of the malkangni oil component by suitably blending malkangni oil with other carrier oil and reducing the content of malkangni oil.

In addition, the composition (M+C) showed a greater decrease in the VAS value after administration than the cypriol oil composition (C), indicating that it has a better pain-relieving effect. Namely, it can be seen that the use of a combination of cypriol oil and malkangni oil is more effective in pain relief than the use of cypriol oil alone.

TABLE 1

Comparison of VAS of pain between before and after administration of composition and comparison of GAS after completion of test

| Composition | Number of patients | Administration period (days) | VAS (pre) | VAS (post) | VAS improvement rate* | GAS |
|---|---|---|---|---|---|---|
| M + C | 17 | 16.6 | 6.5 (±0.2) | 2.8 (±0.3) | 57.01 (±4.8)% | 2.4 (±0.3)** |
| C | 5 | 16.4 | 6.3 (±0.3) | 3.3 (±0.3) | 48.16 (±3.9)% | 1.8 (±0.4) |
| M | 5 | 15.4 | 6.7 (±0.3) | 3.7 (±0.3) | 44.26 (±3.0)% | 1.0 (±0.3) |

*VAS improvement rate = the absolute value of VAS(post) − VAS(pre)/VAS(pre) expressed as percentage (%).
**The number of patients of the (M + C) groups for GAS was 14.

The values in the Table are expressed as mean (±standard error).

The results of GASs assessed by the patients were similar to the change rates in the VASs (see Table 1 and FIG. 3). The group administered with the composition (M+C) showed the highest GAS value, and the group administered with the cypriol oil composition (C) showed the second higher GAS value, and the group administered with the composition (M) including malkangni oil alone showed the lowest GAS value. The degree of pain felt by the patients was the highest in the group administered with the composition (M+C), similar to the VAS.

(2) Comparison of Feeling of Use after Administration of Compositions

After completion of the administration duration of the composition (M) including malkangni oil alone, the cypriol oil composition (C), and the composition including a combination of malkangni oil and cypriol oil, the feeling of use of the compositions was comparatively analyzed. Table 2 below shows the degree of stickiness, the degree of skin absorption and the index of feeling of use after skin application of each composition.

The results of the feeling of use evaluated by the patients were also similar to the VAS or GAS results. Namely, it was shown that the group administered with the composition (M+C) showed the highest degree of skin absorption and the lowest stickiness, indicating that it gives the best feeling of use among the three compositions. The skin absorption rate in the group administered with the cypriol oil composition (C) was lower than but did not significantly different from that in the group administered with the composition (M+C), whereas the change in the VAS value between before and after administration was much more significant than the difference in the skin absorption rate (see Table 1). In view of this fact, it can be seen that the difference in the pain-relieving effect between the two compositions is not attributable to the difference in the skin absorption rate between the compositions, but is attributable to the difference in the components between the compositions. That is, the use of a combination of cypriol oil and malkangni oil has an improved pain-relieving effect compared to the use of cypriol oil alone.

Finally, it was shown that the group administered with the composition (M) including malkangni oil showed the highest stickiness and the lowest skin absorption among the three compositions. This Example confirmed again that the use of a combination of malkangni oil and other carrier oil is more advantageous in terms of pain relief or the feeling of use than the use of malkangni oil alone.

TABLE 2

Comparison of feeling of use between compositions

| Composition | Degree of stickiness | Degree of skin absorption | Feeling of use (overall) |
|---|---|---|---|
| M + C | 0.9 (±0.2) | 3.9 (±0.2) | 4.6 (±0.1) |
| C | 1.2 (±0.4) | 3.6 (±0.5) | 4.0 (±0.3) |
| M | 4.0 (±0.4) | 1.0 (±0.4) | 1.8 (±0.4) |

The values in Table 2 above are expressed mean±standard error.

Preparation Examples

1. Preparation of Formulations for Skin Application
(1) Gel

According to the exemplary embodiments, a gel may include the following composition of active ingredients. The gel may be prepared according to a conventional method used for formulating gel for the skin application.

| Malkangni oil | 5 wt % |
|---|---|
| Cypriol oil | 10 wt % |
| Lavender oil | 2 wt % |
| Jojoba oil | 15 wt % |
| Sodium acetate ethylenediamine | 0.05 wt % |
| Glycerin | 5.0 wt % |
| Carboxyvinyl polymer | 0.3 wt % |
| Ethanol | 5.0 wt % |
| PEG-60 hydrogenated castor oil | 0.5 wt % |
| Triethanolamine | 0.3 wt % |
| Preservative | 0.05 wt % |
| Purified water | up to 100 wt % |

(2) Ointment

According to the exemplary embodiments, an ointment may include the following composition of active ingredients. The ointment may be prepared according to a conventional method used for formulating gel for the skin application.

| Malkangni oil | 5 wt % |
|---|---|
| Cypriol oil | 5 wt % |
| Lavender oil | 2 wt % |
| Beta-1,3-glucan | 10.0 wt % |
| Beeswax | 10.0 wt % |
| Polysorbate 60 | 5.0 wt % |
| PEG-60 hydrogenated castor oil | 2.0 wt % |
| Sorbitan sesquioleate | 0.5 wt % |
| Vaseline | 5.0 wt % |
| Liquid paraffin | 10.0 wt % |
| Squalan | 5.0 wt % |
| Shea butter | 3.0 wt % |
| Caprylic/capric triglyceride | 5.0 wt % |
| Glycerin | 10.0 wt % |
| Propylene glycol | 10.2 wt % |
| Triethanolamine | 0.2 wt % |
| Preservative | 0.05 wt % |
| Pigment | 0.05 wt % |
| Purified water | up to 100.0 wt % |

(3) Medicament for Topical Administration (Patch)

According to the exemplary embodiments, a medicament for topical administration may include the following composition of active ingredients. The medicament for topical administration may be prepared according to a conventional method used for formulating gel for the skin application.

| Malkangni oil | 5 wt % |
|---|---|
| Cypriol oil | 5 wt % |
| Chamomile oil | 3 wt % |
| Beta-1,3-glucan | 3.0 wt % |
| Hexylene glycol | 20.0 wt % |
| Diethylamine | 0.7 wt % |
| Polyacylic acid (Carbopol [0256 [934P]) | 1.0 wt % |
| Sodium sulfite | 0.1 wt % |
| Polyoxyethylene lauryl ether (E.O. = 9) | 1.0 wt % |
| Polyhydroxyethylene cetyl stearyl ether (Cetomacrogol 1000) | 1.0 wt % |
| Viscous paraffin oil | 2.5 wt % |
| Caprylic ester/capric ester (Cetiol LC) | 2.5 wt % |
| Polyethylene glycol 400 | 3.0 wt % |
| Deionized water | up to 100 wt % |

2. Preparation of Cosmetic Formulations
(1) Massage Cream

According to the exemplary embodiments, a massage cream may include the following composition of active ingredients. The massage cream may be prepared according to a conventional method used for formulating gel for the skin application.

| Malkangni oil | 2 wt % |
|---|---|
| Cypriol oil | 4 wt % |
| Lavender oil | 1 wt % |
| Jojoba oil | 20 wt % |
| Beta-1,3-glucan | 3.0 wt % |
| Beeswax | 10.0 wt % |
| Polysorbate 60 | 1.5 wt % |
| PEG-60 hydrogenated castor oil | 2.0 wt % |
| Sorbitan sesquioleate | 0.8 wt % |
| Liquid paraffin | 40.0 wt % |
| Squalan | 5.0 wt % |
| Caprylic/capric triglyceride | 4.0 wt % |
| Glycerin | 5.0 wt % |
| Butylene glycol | 3.0 wt % |
| Propylene glycol | 3.0 wt % |
| Triethanolamine | 0.2 wt % |
| Preservative | 0.05 wt % |
| Pigment | 0.05 wt % |
| Purified water | up to 100 wt % |

(2) Preparation of Skin Mask

According to the exemplary embodiments, a skin mask may include the following composition of active ingredients. The skin mask may be prepared according to a conventional method used for formulating gel for the skin application.

| | |
|---|---|
| Malkangni oil | 2 wt % |
| Cypriol oil | 2 wt % |
| Chamomile oil | 0.5 wt % |
| Jojoba oil | 10 wt % |
| Beta-1,3-glucan | 1.0 wt % |
| Polyvinyl alcohol | 13.0 wt % |
| Sodium carboxymethylcellulose | 0.2 wt % |
| Glycerin | 5.0 wt % |
| Allantoin | 0.1 wt % |
| Ethanol | 6.0 wt % |
| PEG-12 nonyl phenyl ether | 0.3 wt % |
| Polysorbate-60 | 0.3 wt % |
| Preservative | 0.05 wt % |
| Pigment | 0.05 wt % |
| Purified water | up to 100 wt % |

As described above, the composition including malkangni oil and cypriol oil according to the exemplary embodiments is useful for the development of medicaments, formulations for skin application and cosmetic formulations for treating pain, which have a very low risk of causing side effects, such as toxicity or addiction, have improved sensory properties and improved feeling of use, and are effective and safe.

Therefore, the exemplary embodiments provides a pharmaceutical composition for treating pain, a composition for skin application and a cosmetic composition for relieving pain, each including malkangni oil and cypriol oil. The compositions according to the exemplary embodiments further improve the pain-killing effects of malkangni oil and cypriol oil, improve the feeling of use and sensory feeling of malkangni oil and cypriol oil, and are quickly absorbed into the skin without stickiness. Thus, these compositions have the effect of effectively relieving pain.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A pharmaceutical composition for relieving pain, the pharmaceutical composition comprising malkangni oil and cypriol oil as active ingredients wherein a weight ratio of the malkangni oil to the cypriol oil is 1:0.1 to 1:10.

2. The pharmaceutical composition of claim 1, further comprising a carrier oil.

3. The pharmaceutical composition of claim 2, wherein a weight ratio of the malkangni oil to the carrier oil is 1:0:1 to 1:99.

4. The pharmaceutical composition of claim 2, wherein the carrier oil comprises at least one selected from the group consisting of almond oil, sweet almond oil, olive oil, castor oil, jojoba oil, avocado oil, apricot kernel oil, borage oil, *Calendula* oil, carrot seed oil, cocoa butter, evening primrose oil, grape seed oil, hazelnut oil, walnut oil, pecan nut oil, macadamia nut oil, peanut oil, rosehip seed oil, sesame seed oil, flaxseed oil, sunflower seed oil, *Camellia* seed oil, marula oil, safflower oil, canola oil, soybean oil, wheat germ oil, marigold oil, lime blossom oil, coconut oil, *Arnica* oil, shea butter, and peach kernel oil.

5. The pharmaceutical composition of claim 1, further comprising a vegetable essential oil.

6. The pharmaceutical composition of claim 5, wherein a weight ratio of the malkangni oil to the vegetable essential oil is 1:0.1 to 1:10.

7. The pharmaceutical composition of claim 6, wherein the vegetable essential oil comprises at least one selected from the group consisting of *Cassia* bark oil, lemon oil, lemongrass oil, lavender oil, rosemary oil, sweet orange oil, bergamot oil, mandarin oil, star anise oil, cinnamon oil, ginger oil, *Cananga* oil, ylang oil, cajeput oil, clove oil, patchouli oil, peppermint oil, spearmint oil, *Mentha arvensis* oil, frankincense oil, myrrh oil, roman chamomile oil, German chamomile oil, sweet majoram oil, geranium oil, jasmine oil, *Eucalyptus* oil, black pepper oil, and *Helichrysum* oil.

8. The pharmaceutical composition of claim 1, wherein a weight ratio of the malkangni oil to the cypriol oil is 1:2.

9. The pharmaceutical composition of claim 1, wherein the malkangni oil and the cypriol oil collectively comprise at least 10 weight percent of the total weight percent of the pharmaceutical composition.

10. A cosmetic composition for relieving pain, the cosmetic composition comprising malkangni oil extracted from the seed *Celastrus paniculatus* and cypriol oil extracted from the tuber of *Cyperus scariosus* as active ingredients wherein a weight ratio of the malkangni oil to the cypriol oil is 1:0.1 to 1:10.

11. The cosmetic composition of claim 10, wherein the malkangni oil and the cypriol oil collectively comprise at least 10 weight percent of the total weight percent of the pharmaceutical composition.

12. The cosmetic composition of claim 10, wherein a weight ratio of the malkangni oil to the cypriol oil is 1:2.

13. A method of topical administration of a pharmaceutical composition on skin for relieving pain, the method comprising:
locally applying the pharmaceutical composition on an area of skin corresponding to the pain,
wherein the pharmaceutical composition comprising malkangni oil and cypriol oil as active ingredients wherein a weight ratio of the malkangni oil to the cypriol oil is 1:0.1 to 1:10.

14. The method of claim 13, wherein the pain is acute pain or chronic pain.

15. The method of claim 13, wherein the pain is associated with one or more selected from among diabetic neuropathy, diabetic peripheral neuropathy, pain caused by viral infection, nociceptive pain, facial neuralgia, postherpetic neuralgia, low back pain, disc pain, radiculopathy, neuropathy, hyperalgesia, central sensitization-related pain, allodynia, cancer pain, myofascial pain syndrome, Carpal tunnel syndrome, cubital tunnel syndrome, DeQuervain syndrome, rotator cuff syndrome, osteoarthritis, tendinitis, peritenonitis, lateral epicondylitis, medial epicondylitis, tendon injury, bursitis, syndesmitis, tennis elbow, golf elbow, knee arthralgia, tendinitis around knee, semilunar cartilage injury, finger arthralgia, wrist tendinitis, wrist sprain, ankle sprain, sprain, fibromyalgia, plantar fasciitis, inflammatory arthritis, infectious arthritis, rheumatoid arthritis, degenerative joint pain, frozen shoulder, gout, postnatal joint pain, osteomyelitis, ankylosing spondylitis, degenerative spinal lesion, lumbar spinal stenosis, cruralgia, sprain, bruise, arthralgia, and sciatica.

16. The method of claim 13, wherein a weight ratio of the malkangni oil to the cypriol oil is 1:2.

17. The method of claim 16, wherein the pharmaceutical composition further comprises a carrier oil.

18. The method of claim 17, wherein a weight ratio of the malkangni oil to the carrier oil is 1:0.1 to 1:99.

19. The method of claim 16, wherein the pharmaceutical composition further comprises a vegetable essential oil.

20. The method of claim 19, wherein a weight ratio of the malkangni oil to the vegetable essential oil is 0.1:10 to 1:10.

* * * * *